United States Patent [19]
Haddock

[11] Patent Number: 6,004,308
[45] Date of Patent: Dec. 21, 1999

[54] ADHESIVE ATTACHMENT SYSTEM WITH A NON-TACKY SURFACE FOR SANITARY NAPKINS

[75] Inventor: Teresa Haddock, Cranbury, N.J.

[73] Assignee: McNeil-PPC, Inc., Skillman, N.J.

[21] Appl. No.: 08/636,472

[22] Filed: Apr. 19, 1996

[51] Int. Cl.$^6$ .............................. A61F 13/16; A61L 15/58
[52] U.S. Cl. .......................... 604/390; 604/389; 428/343; 428/355
[58] Field of Search ...................... 604/386, 387, 604/389, 390; 428/343, 355, 373, 99, 100; 524/462, 463, 474, 504, 903

[56] References Cited

U.S. PATENT DOCUMENTS

| | | | |
|---|---|---|---|
| 4,735,837 | 4/1988 | Miyasaka et al. | 428/40 |
| 5,045,569 | 9/1991 | Delgado | 521/60 |
| 5,378,536 | 1/1995 | Miller et al. | 428/355 |

*Primary Examiner*—Ronald Stright
*Assistant Examiner*—David J. Cho
*Attorney, Agent, or Firm*—James P. Barr

[57] ABSTRACT

This invention is directed to a pressure sensitive positioning adhesive for absorbent articles which can be used without release paper. The positioning adhesive has non-tacky irregularly shaped particles on its surface thereby rendering the adhesive non-tacky. Upon the application of pressure during use, i.e., when attaching the napkin to the undergarment, the particles are rearranged, exposing adhesive to the undergarment, thereby facilitating attachment of the napkin to the undergarment.

33 Claims, 5 Drawing Sheets

ADHESIVE ATTACHMENT SYSTEM WITH A NON-TACKY SURFACE FOR SANITARY NAPKINS

FIELD OF THE INVENTION

This invention relates to the field of sanitary absorbent articles and more particularly, to the use of a reversibly detackified adhesive system on the garment facing surfaces of a sanitary absorbent article which enables a user of the article to secure the article to their undergarment during use.

BACKGROUND OF THE INVENTION

Disposable absorbent articles conventionally have a layer of pressure sensitive adhesive on their garment facing surfaces to enable the user's of these articles to secure the article into their undergarment. The pressure sensitive adhesive sticks to various substrates upon contact with the application of a small amount of pressure and thereby prevents the article from shifting during the time the article is in use. A release paper is often used to protect the adhesive before the application of the napkin to the wearer's undergarment.

For disposable absorbent articles, cost and convenience are important factors for both the consumer and the manufacturer. The use of a silicone treated release paper to cover adhesive surfaces on disposable absorbent articles contributes significantly to the cost of the article. In addition, when the article is used by a consumer, the release paper is no longer needed and must be discarded, which creates environmental problems as well as an inconvenience to the consumer.

Currently, there are some sanitary napkin articles that do not use a release paper. However, the adhesive surfaces of these napkins are protected by wrapping the napkin in polymeric film which has also been treated with a silicone release coating. The silicone treated polymeric film is releasably adhered to the adhesive surface to protect it from contamination and to prevent the napkins from adhering to surfaces prior to their intended use. Since these polymeric film materials are also treated with a silicone release coating there are no significant cost savings compared to the use of release paper and the environmental and convenience factors are still present.

SUMMARY OF THE INVENTION

It is an object of this invention to provide a cost effective sanitary absorbent article which is also user friendly.

It is another object of the present invention to provide a protection system other than conventional release paper for a pressure sensitive adhesive positioning adhesive on a sanitary napkin.

It is another object of this invention to provide an absorbent article having positioning adhesive on a garment facing surface thereof which does not require the presence of a release paper.

In accordance with the present invention, there has now been provided an absorbent article having an absorbent body-facing surface, a fluid impervious garment-facing surface, a layer of pressure sensitive hot melt adhesive on at least a portion of the garment-facing surface, and a layer of non-tacky irregularly shaped particles adhered to the pressure sensitive hot melt adhesive in an amount effective to detackify the pressure sensitive hot melt adhesive upon the application of low pressure thereto.

DETAILED DESCRIPTION OF THE INVENTION

Figure 1:
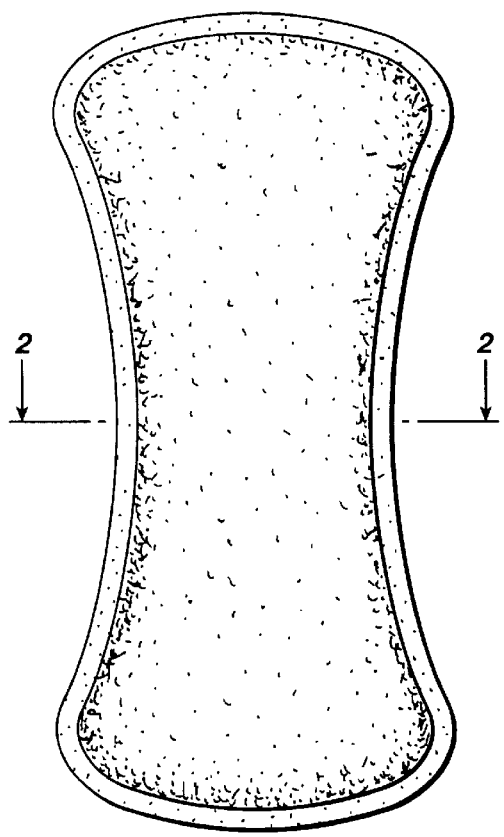
FIG. 1 shows a plan view of a sanitary napkin.

The present invention is directed to an absorbent article which employs a reversibly detackified hot melt pressure sensitive adhesive system as a positioning adhesive on a garment facing surface of the absorbent article. In accordance with this invention, at least a portion of a garment facing surface of a sanitary absorbent article is coated with a hot melt pressure sensitive adhesive. The surface of the hot melt pressure sensitive adhesive is protected by a layer of non-tacky irregularly shaped particulate material instead of a conventional sheet of release paper which reversibly detackifies the adhesive surface. As used herein, the terminology 'reversibly detackify' refers to a hot melt pressure sensitive adhesive having non-tacky irregularly shaped particulate matter adhered to its surface and which, upon the application of light pressure does not adhere or only weakly adheres to the source of the light pressure, but which is capable of adhering to the source of moderate pressure against the adhesive surface. As used herein the terminology 'moderate pressure' refers to an amount of pressure which is sufficient to displace or submerge the non-tacky irregularly shaped particulate matter into the layer of hot-melt adhesive and thereby expose at least a portion of the garment facing surface of the hot-melt adhesive to the source of the pressure. This terminology also refers to an amount of pressure which when applied to a fabric material is sufficient to cause the fibers of the fabric material to enter into interstices between the non-tacky irregularly shaped particulate matter and thereby contact and adhere to the underlying adhesive. Alternatively, this terminology includes the amount of pressure which is required to deform malleable non-tacky irregularly shaped particulate matter such as wax particles or the like thereby exposing at least a portion of the surface of the underlying adhesive.

The reversibly detackified adhesive system of this invention may be used on any absorbent articles which are intended to be adhesively adhered during use, and include sanitary napkins, panty liners, adult incontinence devices, and the like. In their simplest form the absorbent articles of the present invention comprise a fluid pervious, absorbent body-facing surface, a fluid impervious garment-facing surface, a layer of pressure sensitive adhesive on at least a portion of the garment-facing surface, and a layer of non-tacky irregularly shaped particles adhered to the pressure sensitive hot melt adhesive in an amount effective to detackify the pressure sensitive adhesive upon the application of moderate pressure thereto. When used as a positioning adhesive on a sanitary napkin, the hot-melt adhesive may be directly or indirectly coated onto the garment facing fluid impervious barrier film, onto the side tabs, or any other component where adhesives are conventionally applied. In a typical sanitary napkin, the positioning adhesive is applied to a garment facing surface of the sanitary napkin in an amount sufficient to provide a thickness of about 1 to 10 mils, preferably 1 to 5 mils and most preferably 1 to 3 mils and a surface area sufficient to maintain the sanitary napkin in the user's undergarment without loosening or shifting about. In general, a sufficient surface area ranges from about 4 to 8 sq. inches for small sanitary napkins to about 8 to 20 sq. inches for full size sanitary napkins. Suitable garment-facing surfaces include a central body portion of the sanitary absorbent article which underlies a central absorbent core and/or includes flaps, tabs or cuffs which extend laterally from the longitudinal edges of the central body portion of the sanitary napkin.

Suitable adhesives for use in this invention generally include any pressure sensitive adhesives which provide a releasable bond between two surfaces and generally include solvent based pressure sensitive adhesives, water-based pressure sensitive adhesives and hot-melt type pressure sensitive adhesives, and are preferably hot-melt type of pressure sensitive adhesives. Suitable solvent based pressure sensitive adhesives, water-based pressure sensitive adhesives and hot-melt pressure sensitive adhesives are well known to those skilled in the art and the particular choice of a pressure sensitive adhesive is not, per se, critical to the invention provided of course that the adhesive does not cause irritation to the wearer of the absorbent article and that the adhesive is compatible with the conventional garment facing barrier layer materials which are used to make absorbent articles. As used herein, the terminology 'compatible' refers to those materials which do not deleteriously effect the components in the absorbent article or the intended use of the absorbent article. For example a compatible adhesive should not be capable of dissolving a polyolefin barrier layer of the absorbent article or otherwise negatively affecting the performance of the absorbent article such as by forming a permanent bond between a wearer's undergarment and the absorbent article. Examples of suitable pressure sensitive adhesives include, but are not limited to synthetic rubber-like formulated materials such as styrene-isoprene-styrene (SIS) block copolymers which are commercially available under the trade name KRATON 1107 from the Shell Oil Company, VECTOR 4113, VECTOR 4211 form the Dexco Company, styrene-ethylene-butylene-styrene (SEBS) block copolymers which are commercially available under the trade name KRATON G from the Shell Oil Company, styrene-butylene-styrene (SBS) block copolymers which are commercially available under the KRATON D-1101 and D-1300 from the Shell Oil Company, and combinations thereof. These polymeric adhesives may be formulated with tackifier resin such as a hydrocarbon resin or rosin esters as tackifier to increase the tackiness of the adhesive. Examples of common tackifier resins include, for example, C5–C9 hydrocarbon resins which are commercially available from the Goodyear Company under the trade name WINGTACK or from the Exxon Corporation under the trade name ESCOREZ 2595. The adhesives of this invention may also be formulated with oil, such as for example mineral oil, as a plasticizer for viscosity modification. These adhesives are more fully disclosed in U.S. Pat. Nos. 5,149,741, 4,419,449 and 4,526,577 which are incorporated herein by reference in their entirety. A preferred pressure sensitive adhesive is one that is relatively malleable, i.e. permits the non-tacky irregularly shaped particulate matter to be easily displaced or submerged into the surface of the pressure sensitive adhesive.

After the adhesive has been applied to the article, it is then coated with the non-tacky irregularly shaped particles. As used herein the terminology 'non-tacky' refers to particulate materials which may be adhered to the surface of the hot-melt adhesive to prevent the hot-melt adhesive from adhering to surfaces upon the application of light pressure thereto but which may possess some weak adhesive properties. A weak adhesive property is one where the non-tacky irregularly shaped particulate material is capable of adhering to a surface but which is removable from that surface without causing damage or distortion to the surface. An example of a weak adhesive property is the ability of a material to adhere to a polyethylene wrapping film and which is removable without tearing or distorting the polyethylene film material. The amount of non-tacky irregularly shaped particles adhered to the surface of the hot melt pressure sensitive adhesive should be sufficient to detackify the surface of the positioning adhesive. This amount may be equal to the theoretical amount required to completely cover the entire surface area of the positioning adhesive or may be significantly less than this amount depending, of course, on the size of the particles used and the degree of detackification desired. It is preferred that the amount of particles be less than the theoretical amount which would be necessary to completely cover the surface area of the adhesive, and is most preferably in an amount which is less than 90% of the total surface area of the adhesive. The particles can be applied by a powder coating process or can be simply sprayed onto the adhesive surface on a moving web.

It is considered an important feature of the present invention that the reversibly detackified pressure sensitive adhesive provide a relatively strong bond between the absorbent article and the garment to which the absorbent article is intended to be attached. A suitable bond strength between the absorbent article and the garment is generally at least 0.2 lb., and is preferably at least 0.3 lb., and is most preferably at least 0.5 lb. as measured by a standard peel test. The above described pressure sensitive adhesives will provide a bond strength in the above ranges when applied at about 10 mg. per sq. inch to 100 mg per sq. inch. A standard peel test is a measure of the peel force between a cotton substrate and the hot melt pressure sensitive adhesive is measured using the standard 12"/min., 180 degree peel angle procedure.

The standard peel test method is commonly used to determine the average force per adhesive strip width required to peel a piece of cotton fabric from the pressure sensitive adhesive positioning adhesive of a sanitary napkin pad. In accordance with this test an 80 by 80 standard bleached woven cotton cloth having a width sufficient to cover the adhesive width is placed on the surface of the adhesive to form a laminate. A 10 lb. roller is place on top of the laminate and rolled back and forth once at a constant speed of 12"/min. to create an adhesive bond between the pressure sensitive adhesive and the cotton. The laminate is allowed to condition for 30 minutes whereupon the cotton is then peeled away at a 180 degree angle at a rate of 12 inches per minute. The amount of force required to peel the cotton cloth from the adhesive may be measured on an Instron tester or any other conventional type of peel tester.

Suitable non-tacky irregularly shaped particles for use in the present invention include any non-tacky irregularly shaped particulate matter which sufficiently detackifies the pressure sensitive adhesive to prevent permanent adherence to a surface but which does not deleteriously affect the bond strength between the pressure sensitive adhesive and the surface to which it is intended to be applied. In general, suitable non-tacky irregularly shaped particulate matter has a particle size in a range of from about 1 micron to about 2500 microns. The non-tacky irregularly shaped particles may be organic, inorganic or a mixture of organic and inorganic particles.

Suitable organic particulate materials include polymers as well as relatively low molecular weight organic materials. Suitable polymeric particles include non-acrylic polymers including but not limited to amorphous polypropylene homopolymers, polypropylene-ethylene copolymer, propylene-butene copolymers, propylene-hexene copolymers, propylene-butene-ethylene terpolymers. polyethylene based adhesives, ethylene/vinyl acetate (EVA) resins polystyrene, polyethylene, polypropylene, PTFE polymers (such as e.g. TEFLON®), polyvinyl chloride (PVC), low molecular weight polyethylene waxes, starch particles such as that derived from corn, etc. It is considered important that the non-tacky irregularly shaped organic particulate material used to coat the surface of the adhesive not be soluble in the adhesive, and that it have a melting point above normal storage temperatures of the absorbent article. Preferred organic particles are soft or malleable, i.e. they are easily deformed upon the application of moderate pressure. A particularly preferred non-tacky irregularly shaped particulate material comprises polyethylene particles having an average particle diameter in the range of from 1 to 2500 microns, preferably in the range of from 5 microns to 1500 microns and most preferably in the range of from 10 microns to 90 microns. Examples of suitable commercially available products include, but are not limited to E-804 and A-776S from the Eastman Company, HL 1308, HL1094 from the Fuller Company, and the like.

The organic non-tacky particles of this invention may advantageously be applied to the pressure sensitive adhesive as either solid particles using conventional powder coating techniques or in a liquid state, such as e.g. when the non-tacky particles are at elevated temperatures, using conventional liquid coating techniques such as e.g. a rotary screen coating process. When applied in a liquid state, it is preferred that the organic material have a viscosity in a range of between 100 cps and 100,000 cps at 350 deg. F. In addition, when the organic non-tacky particles are applied in a liquid state, they may be sprayed onto the adhesive layer in the form of discrete, non-tacky dots or alternatively may be sprayed in a continuous or discontinuous thin line across the surface of the adhesive. The above described organic materials may be formulated with various waxes or oils to obtain a material having a viscosity in the above preferred range.

Suitable inorganic non-tacky irregularly shaped particulate materials include, but are not limited to particles of silica, alumina, talc, glass, ground calcium carbonate, zeolites, and the like and combinations thereof. A particularly preferred inorganic material is talc having an average particle diameter in the range of from 20 to 150 micron, and preferably in the range of from 60 to 90 micron.

In a first embodiment of the invention, a layer of pressure sensitive adhesive is applied to a garment facing surface of a sanitary absorbent article. The layer of adhesive may be applied as a generally uniform thickness over the entire central body portion and or tabs, or optionally may be applied as discrete strips in a variety of patterns such as strips which are generally parallel to a longitudinal axis of the sanitary absorbent article, or may be strips which are generally orthogonal to a longitudinal axis of the sanitary absorbent article, or may be oriented in an 'X' configuration wherein a first adhesive strip begins in a first corner of the sanitary absorbent article and continues diagonally across a longitudinal centerline to a corner on an opposite side of the sanitary absorbent article. Alternatively, the adhesive pattern may be a series of discrete spaced apart elements, i.e. adhesive patterns in a variety of geometric shapes such as dots, ovals, circles, semi-circles, rectangles, squares, chevrons, diamonds, and the like, and combinations thereof, which may be in a predetermined pattern or randomized over all or a portion of the garment facing surface of the sanitary absorbent article.

The layer of pressure sensitive adhesive is then covered with a layer of non-tacky irregularly shaped particles having average particle sizes (i.e. diameters) which are less than the thickness of the adhesive layer. The layer of non-tacky irregularly shaped particles applied to the adhesive layer is in an amount effective to inhibit the pressure sensitive from adhering to a surface upon the application of low pressure to the adhesive. Suitable amounts of non-tacky irregularly shaped particles which may be applied to the surface of the pressure sensitive adhesive can range from 10 to 90% of surface area, and is preferably in the range of from 30 to 70% of surface area.

The average particle size should be less than the thickness of the adhesive layer and generally ranges from between 10% to 90% of the adhesive film thickness, preferably in a range of between 15% and 85% of the adhesive thickness, and most preferably in a range of from 20% to 75% of the adhesive thickness.

Upon application of moderate pressure during use, i.e., when the sanitary napkin is applied to the wearer's undergarment, due to the inherent malleability of the adhesive, the particles will submerge into the adhesive layer and thus expose the surface of the pressure sensitive adhesive to the fibers of the undergarment to enable the formation of an adhesive bond between the napkin and the undergarment. In accordance with this embodiment, it has been found that the application of about 10 PSI pressure to the napkin is sufficient to displace or submerge the particles into the pressure sensitive adhesive, thereby exposing the surface of the pressure sensitive adhesive to the fibers of the undergarment which forms a releasable bond with the undergarment.

Figure 2:
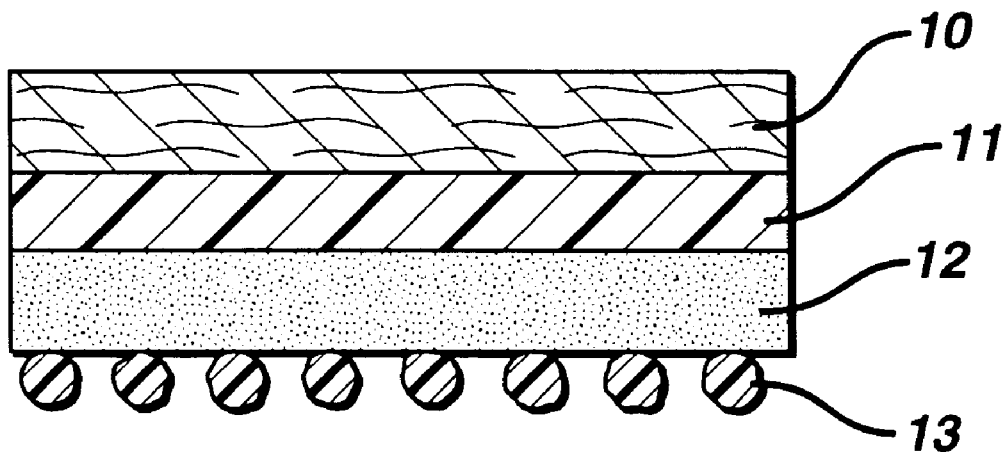
FIG. 2 shows a cross-sectional view of the napkin of the first embodiment of the invention taken along the line 2—2 of FIG. 1.
Figure 3:
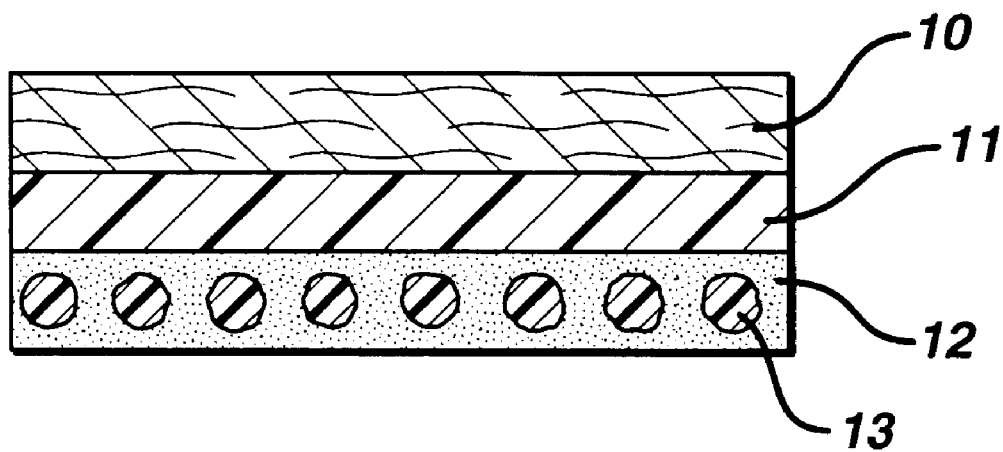
FIG. 3 shows a cross-sectional view of the napkin of the first embodiment of the invention taken along the line 2—2 of FIG. 1.

The mechanism of this embodiment is depicted in FIGS. 2–3. FIG. 1 shows a plan view of a sanitary napkin. FIG. 2 shows a cross-sectional view of the napkin of the first embodiment of the invention. The napkin is comprised of an absorbent core 10 which may optionally be covered by a fluid-pervious cover, a fluid-impervious barrier film 11 and an adhesive layer 12. The adhesive layer has non-tacky irregularly shaped particles having an average particle size which is less than the thickness of the adhesive which are embedded in its surface to render it non-tacky. Upon contact with the wearer's undergarment and upon the application of moderate pressure, the relatively small diameter particles are driven into the adhesive layer, thereby permitting contact between the exposed adhesive surface and the undergarment and thus forming a releasable adhesive bond between the napkin and the undergarment.

In a second embodiment of the invention, the average particle size is greater than or equal to the thickness of the adhesive layer, and is generally in a range of from 100% to 200% of the thickness of the adhesive layer, preferably from 105% to 150% of the thickness of the adhesive layer, and most preferably in a range of from 110% to 140% of the thickness of the adhesive layer. In this embodiment, the particles are applied in an amount such that the particles do not completely cover the surface of the adhesive but in an amount which is sufficient to render the surface of the adhesive non-tacky to the touch at low pressures. In accordance with this aspect of the invention, when a user of the absorbent article applies moderate pressure between an undergarment and the reversibly detackified adhesive coated barrier layer, the fibers of the undergarment contact and become adhered to the exposed adhesive located in the interparticle interstices and thus form a releasable bond between the undergarment and the absorbent article. In this embodiment, the total coverage area by the particles should be less than about 90% of the adhesive surface area. The coverage area is generally between 10 and 90% of the total adhesive surface area, and is preferably between 30 to 70% of the total adhesive surface area. This amount can vary widely depending, of course, on the characteristics of the adhesive and the desired bond strength. For more aggressive adhesives i.e. where the adhesive has high flow characteristics, the particles should cover a larger percentage of the surface area of the adhesive than would be necessary for a less aggressive adhesive.

Figure 4:
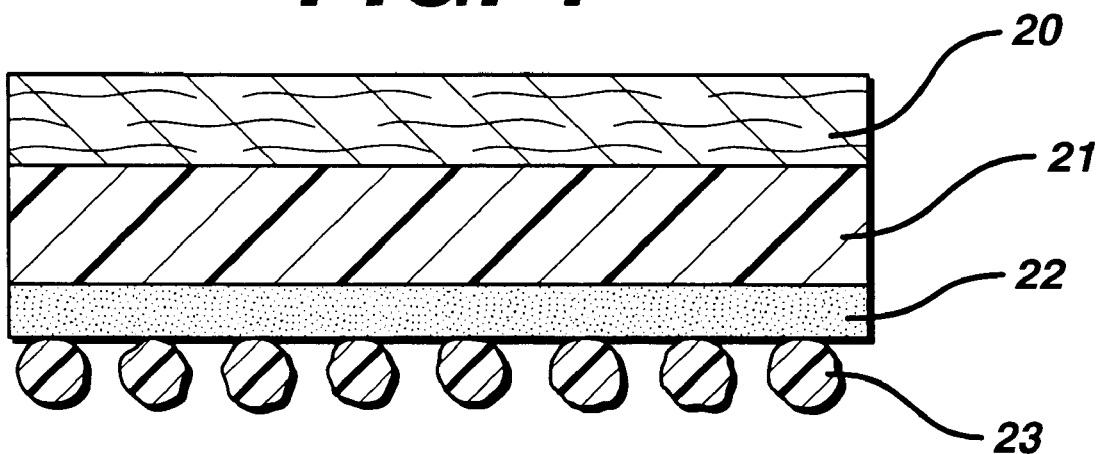
FIG. 4 shows a cross-sectional view of the napkin of the second embodiment of the invention taken along the line 2—2 of FIG. 1.
Figure 5:
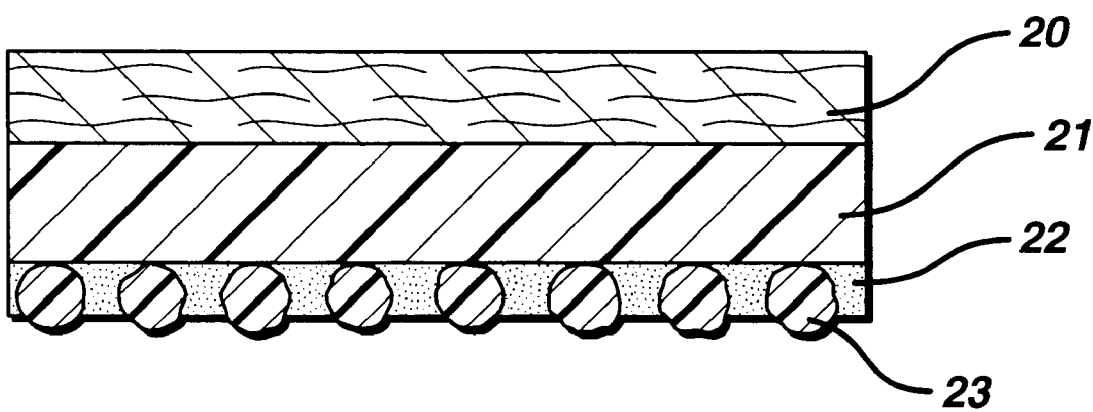
FIG. 5 shows a cross-sectional view of the napkin of the second embodiment of the invention taken along the line 2—2 of FIG. 1.

The mechanism of this embodiment is shown in FIGS. 4 and 5. The napkin in cross-section contains an absorbent layer 20, a barrier layer 21 and a positioning adhesive layer 22. The non-tacky irregularly shaped particles 23 are larger than the thickness of the positioning adhesive. Upon the application of moderate pressure during use, the particle will be partially submerged into the adhesive layer. Since the particles are larger than the thickness of the adhesive, even after the application of moderate pressure, a portion of the particle will continue to extend out of the adhesive surface, however due to the flowability of the hot melt pressure sensitive adhesive, the relatively large particle will displace some of the adhesive thereby surrounding the particle and exposing the adhesive to the source of the pressure. Alternatively, when the source of pressure is a fabric material such as an undergarment, it has been found that the application of moderate pressure to the fabric material causes the fibers in the undergarment 24 to contact and become adhered to the exposed adhesive between adjacent particles. It is of course possible to combine the particles of embodiment one with the particles of embodiment two to form a 'hybrid' reversibly detackified adhesive system containing both large and small particles.

Figure 6:
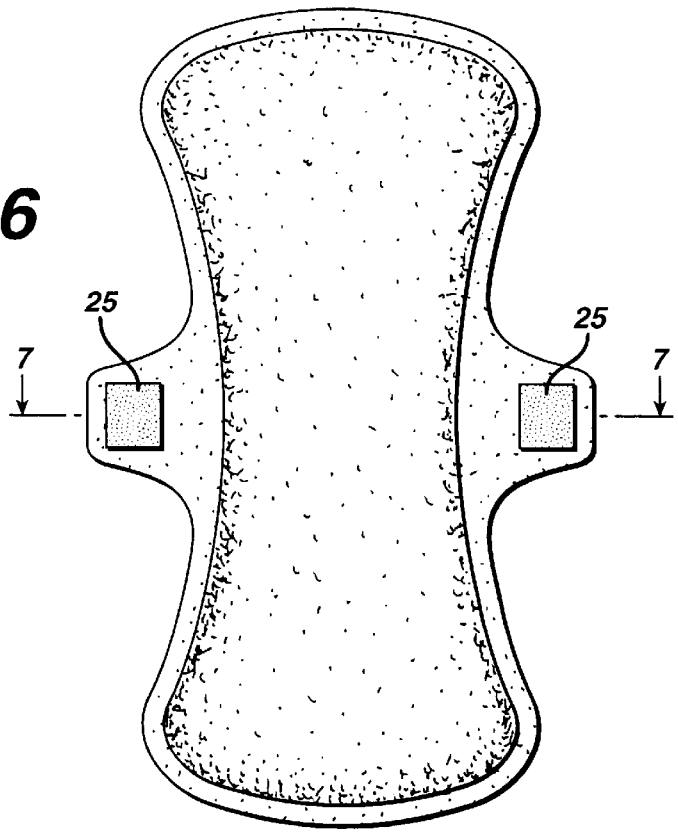
FIG. 6 shows a plan view of a sanitary napkin having tabs extending from its longitudinal sides.
Figure 7:
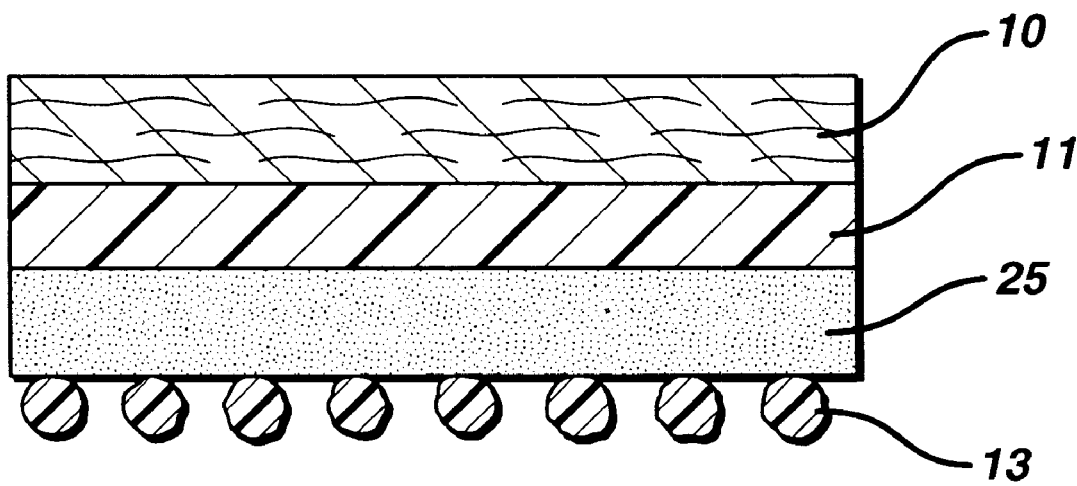
FIG. 7 shows a cross-sectional view of the napkin of the first embodiment of the invention taken along the line 7—7 of FIG. 6.
Figure 8:
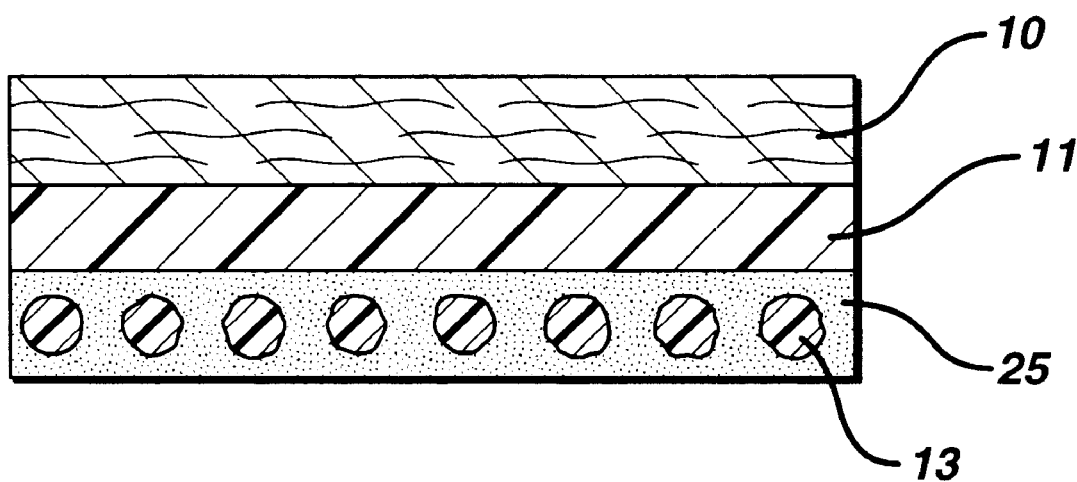
FIG. 8 shows a cross-sectional view of the napkin of the first embodiment of the invention taken along the line 7—7 of FIG. 6.

FIG. 6 illustrates the use of the reversibly detackified adhesive system of the present invention on a sanitary napkin having tabs extending from its longitudinal sides or which are attached inwardly of the sides to the garment facing surface. The regions of adhesive 25 are located on a garment facing surface of the tabs. FIGS. 7 and 8 show a cross-sectional view of the tabs having the reversibly detackified adhesive of the first embodiment of the invention taken along the line 7—7 of FIG. 6. The tabs are comprised of a fluid pervious cover layer 10, a fluid-impervious barrier film 11 and an adhesive layer 25. The adhesive layer has non-tacky irregularly shaped particles having an average particle size which is less than the thickness of the adhesive. The non-tacky irregularly shaped particles are embedded in the adhesive surface to render it non-tacky. In use, the tabs are folded over the edges of the wearer's undergarment and adhered to the underside of the crotch portion of the undergarment. Upon contact with the wearer's undergarment and upon the application of moderate pressure, the relatively small diameter particles are driven into the adhesive layer, thereby permitting contact between the exposed adhesive surface and the undergarment and thus forming an adhesive bond between the tabs on the napkin and the undergarment.

Figure 9:
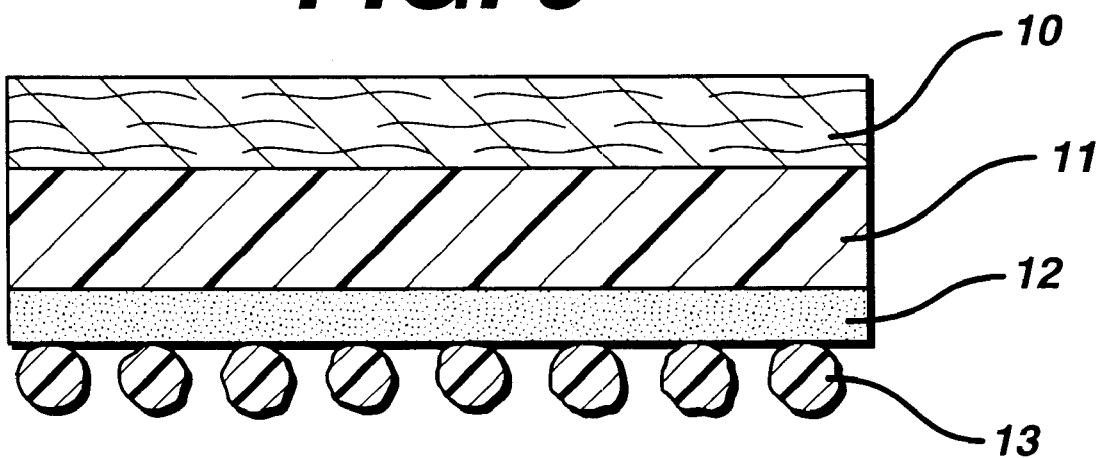
FIG. 9 shows a cross-sectional view of the napkin of the second embodiment of the invention taken along the line 7—7 of FIG. 6.
Figure 10:
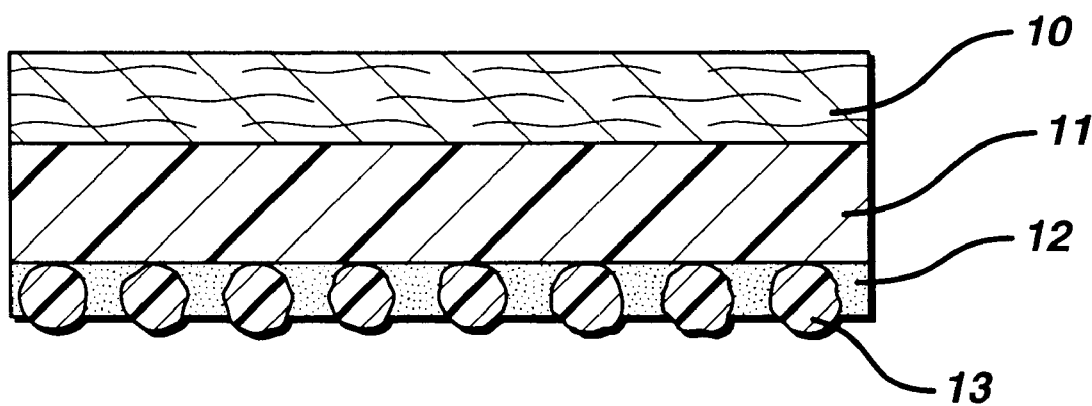
FIG. 10 shows a cross-sectional view of the napkin of the second embodiment of the invention taken along the line 7—7 of FIG. 6.

FIGS. 9 and 10 show a cross-sectional view of the tabs having the reversibly detackified adhesive of the second embodiment of the invention taken along the line 7—7 of FIG. 6. The tabs are comprised of a fluid pervious cover layer 10, a fluid-impervious barrier film 11 and an adhesive layer 25. The adhesive layer has non-tacky irregularly shaped particles having an average particle size which is greater than the thickness of the adhesive. The non-tacky irregularly shaped particles are embedded in the surface of the adhesive to render it non-tacky. In use, the tabs are folded over the edges of the wearer's undergarment and adhered to the underside of the crotch portion of the undergarment. Upon contact with the wearer's undergarment and upon the application of moderate pressure, the relatively large diameter particles are driven into the adhesive layer, thereby permitting contact between the exposed adhesive surface and the undergarment and thus forming an adhesive bond between the tabs on the napkin and the undergarment.

FIGS. 9 and 10 show a cross-sectional view of the napkin of the second embodiment of the invention taken along the line 7—7 of FIG. 6.

Since the napkins are non-tacky upon the application of light pressure, they may be conveniently stacked in boxes or individually wrapped in a polyethylene film to provide a individual packages which do not require the presence of a release paper or silicone treatment of the polyethylene packaging film. If the napkin is individually wrapped, e.g., in a polyethylene pouch, it is important that the amount of adhesive exposure area should not give a high adhesion to the polyethylene pouch film. Under the standard peel test, the adhesion between the pouch film and adhesive should be less than the tear strength of the film. In other words, the adhesive should not tear the pouch film, and preferably does not distort the pad during the separation of the pad from the pouch.

The concept of the invention can be applied to any absorbent article which uses pressure sensitive adhesive as a means of releasably adhering the article to another surface and includes but is not limited to sanitary napkins, wound dressings, surgical drapes, surgical tapes, etc.

The following non-limiting examples are provided to further illustrate the present invention, but are not to be construed as limiting the present invention in any way except as provided in the appended claims.

EXAMPLE 1

A reversibly detackified pressure sensitive adhesive system was applied to polyethylene roll to form a laminated construction of polyethylene film/pressure sensitive adhesive/non-tacky dot. A strong pressure sensitive adhesive (a styrene-isoprene-styrene based adhesive commercially available from the Fuller Company under the trade name HL1417) was directly coated onto the polyethylene film by slot die coating process at a coating temperature of between 300 deg. F to 325 deg. F. The adhesive coating weight was about 10 to 30 mg/sq. in. A random pattern of non-tacky dots were coated directly onto the pressure sensitive adhesive through a rotary screen coating process. The non-tacky dots were made from 1) amorphous polypropylene (commercially available from Eastman under the trade name P1010) or 2)a polyethylene based adhesive (commercially available from Eastman under the trade name 804) The screen had a design of 64 dots per square inch; each dot was 0.05 inches in diameter and had a thickness of about 9/1000 inch. The pressure sensitive adhesive was applied at target coating rate of 15 mg/sq. in. Approximately 30% of the adhesive area was covered by the non-tacky dots. The detackified adhesive system provided a cotton peel adhesion of 5 oz/in which was considered sufficient for holding a sanitary napkin in place.

The polyethylene film having the detackified pressure sensitive adhesive was used as a barrier layer in a sanitary napkin, and the napkin was easily removed from a polyethylene over-wrap pouch without distorting or damaging the barrier layer of the sanitary napkin.

EXAMPLE 2

A reversibly detackified pressure sensitive adhesive system was applied to a polyethylene roll to form a laminated construction of polyethylene film/pressure sensitive adhesive/non-tacky dot. A strong pressure sensitive adhesive (styrene-isoprene-styrene based adhesive commercially available from the Fuller Company under the trade name HL1417) was directly coated onto the polyethylene film by slot die coating process at a coating temperature of between 300 deg. F to 325 deg. F. The pressure sensitive adhesive was applied at coating rate of 10 to 30 mg/sq. in. A random pattern of non-tacky dots was coated directly onto the pressure sensitive adhesive through a spray coating process. The non-tacky dots were made from 1) amorphous polypropylene (commercially available from Eastman under the trade name P1010) or 2) a polyethylene based adhesive (commercially available from Eastman under the trade name 804) The sprayed dots had various sizes of between 50 microns to 1500 microns. The pressure sensitive adhesive was applied at a target coating rate of 35 mg/ sg. in. Approximately 30% of the adhesive area was covered by the non-tacky dots. The reversibly detackified adhesive system provided a cotton peel adhesion of 10 oz/in (0.62 lb./in.) which was considered sufficient for holding a sanitary napkin in place.

The polyethylene film having the detackified pressure sensitive adhesive was used as a barrier layer in a sanitary napkin, and the napkin was easily removed from a polyethylene over-wrap pouch without damaging the barrier layer of the sanitary napkin.

EXAMPLE 3

A reversibly detackified pressure sensitive adhesive system was directly applied to polyethylene roll to form a laminated construction of polyethylene film/pressure sensitive adhesive/non-tacky dot. In this example a strong pressure sensitive adhesive (a styrene-isoprene-styrene based adhesive commercially available from the Fuller Company under the trade name HL1417) was directly coated onto the polyethylene film by slot die coating process at a coating temperature of between 300 deg. F to 325 deg. F. The adhesive coating weight was about 10 to 30 mg/sq. in. A random pattern of non-tacky dots were coated directly onto the pressure sensitive adhesive through a rotary screen coating process. The non-tacky dots were made from a non-tack adhesive (commercially available from the Findley Company under the trade name H9078-01) which were coated on top of the pressure sensitive adhesive at an add-on level of 10 mg/sq. in. The screen had a design of 64 dots per square inch; each dot was 0.05 inches in diameter and had a thickness of about 9/1000 inch. The low tack adhesive covered about 40% of the PA . The polyethylene sheet material was wound into a roll without any release paper and was easily unwound without damaging or distorting the polyethylene film.

The coated polyethylene film material was incorporated into a sanitary napkin pad. The sanitary napkin pad was easily removed from the polyethylene pouch and provided a cotton adhesion of 8 oz/in peel force.

EXAMPLE 4

This example demonstrates the use of corn starch as an organic particle to reversibly detackify a pressure sensitive adhesive. A pressure sensitive adhesive was applied to a polyethylene roll to form a laminated construction of polyethylene film/pressure sensitive adhesive/non-tacky dot. A strong pressure sensitive adhesive (a styrene-isoprene-styrene based adhesive commercially available from the Fuller Company under the trade name HL1417) was directly coated onto the polyethylene film by slot die coating process at a coating temperature of between 300 deg. F to 325 deg. F. The adhesive coating weight was about 10 to 30 mg/sq. In. A corn starch powder, having a particle size of approximately 5 to 20 microns was sprayed directly onto the pressure sensitive adhesive. The corn starch powder covered about 70% of the surface area of the adhesive. The detackified adhesive system provided a cotton peel adhesion of 7.2 oz/in (or 0.45 lb./in) which was considered sufficient for holding a sanitary napkin in place.

The polyethylene film having the detackified pressure sensitive adhesive was used as a barrier layer in a sanitary napkin, and the napkin was easily removed from a polyethylene over-wrap pouch without damaging the sanitary napkin.

I claim:

1. An absorbent article comprising an absorbent body-facing surface, a fluid impervious garment-facing surface, a layer of pressure sensitive adhesive on at least a portion of the garment-facing surface, and a layer of non-tacky irregularly shaped particles adhered to the pressure sensitive adhesive in an amount effective to detackify the pressure sensitive adhesive upon the application of light pressure thereto.

2. The absorbent article according to claim 1 wherein the non-tacky irregularly shaped particles have a particle size in a range of from 1 micron to 2500 microns.

3. The absorbent article according to claim 1 wherein the non-tacky irregularly shaped particles are inorganic particles.

4. The absorbent article according to claim 1 wherein the inorganic particles are selected from the group consisting of silica, alumina, talc, glass, ground calcium carbonate, zeolites, and combinations thereof.

5. The absorbent article according to claim 4 wherein the non-tacky irregularly shaped material have a particle size in a range of from 20 microns to 150 microns.

6. The absorbent article according to claim 4 wherein the non-tacky irregularly shaped material is talc.

7. The absorbent article according to claim 6 wherein the talc particles have an average particle diameter in the range of from 60 to 90 microns.

8. The absorbent article according to claim 6 wherein the talc particles have an average particle diameter in the range of from 60 to 90 microns.

9. The absorbent article according to claim 1 wherein the non-tacky irregularly shaped particles are organic particles.

10. The absorbent article according to claim 1 wherein the organic particles are selected from the group consisting of polystyrene, polyethylene, polypropylene, polytetrafluoroethylene, polyvinyl chloride, polyurethane rubber, polyisoprene rubber, polybutylene rubber, polyethylene waxes, starch and combinations thereof.

11. The absorbent article according to claim 10 wherein the organic particles have an average particle size in a range of from 1 to 2500 microns.

12. The absorbent article according to claim 10 wherein the organic particles have an average particle size in a range of from 5 to 1500 microns.

13. The absorbent article according to claim 10 wherein the organic particles are starch particles.

14. The absorbent article according to claim 13 wherein the starch particles are derived from corn starch having an average particle size in a range of from 5 to 20 microns.

15. The absorbent article according to claim 1 wherein the layer of pressure sensitive adhesive is a styrene-isoprene-styrene based adhesive.

16. The absorbent article according to claim 1 wherein the layer of pressure sensitive adhesive further comprises a tackifier resin and a plasticizer.

17. The absorbent article according to claim 1 wherein the absorbent article has a central body portion and optionally at least one tab extending from a longitudinal edge of the central body portion and wherein the layer of pressure sensitive adhesive is a hot melt pressure sensitive adhesive and wherein the hot melt pressure sensitive adhesive and the layer of non-tacky irregularly shaped particles adhered to the hot melt pressure sensitive adhesive are on a garment-facing side of the central body portion.

18. The absorbent article according to claim 17 wherein the layer of hot-melt adhesive is applied as a generally uniformly thick layer having a thickness of about 1 to 3 mils.

19. The absorbent article according to claim 17 wherein the layer of hot-melt adhesive is applied as discrete strips which are generally parallel to a longitudinal axis of the sanitary absorbent article and wherein the strips have a surface area sufficient to maintain the sanitary napkin in a user's undergarment.

20. The absorbent article according to claim 17 wherein the layer of hot-melt adhesive is applied as discrete strips which are generally orthogonal to a longitudinal axis of the sanitary absorbent article and wherein the strips have a surface area sufficient to maintain the sanitary napkin in a user's undergarment.

21. The absorbent article according to claim 17 wherein the layer of hot-melt adhesive is applied as discrete strips which are oriented in an 'X' configuration wherein a first adhesive strip begins in a first corner of the absorbent article and continues diagonally across a longitudinal centerline to a corner on an opposite side of the absorbent article and wherein the strips have a surface area sufficient to maintain the sanitary napkin in a user's undergarment.

22. The absorbent article according to claim 17 wherein the layer of hot-melt adhesive is applied as a series of discrete elements over at least a portion of the garment facing surface of the absorbent article.

23. The absorbent article according to claim 1 wherein the absorbent article has a central body portion and optionally at least one tab laterally extending from a longitudinal edge of the central body portion and wherein the layer of hot melt pressure sensitive adhesive and the layer of non-tacky irregularly shaped particles adhered to the hot melt pressure sensitive adhesive are on a garment-facing surface of the at least one laterally extending tab.

24. The absorbent article according to claim 1 wherein the non-tacky irregularly shaped particles have an average particle size which is less than the thickness of the adhesive layer.

25. The absorbent article according to claim 24 wherein the non-tacky irregularly shaped particles have an average particle size which is between 10 to 90% of the adhesive thickness.

26. The absorbent article according to claim 1 wherein the non-tacky irregularly shaped particles have an average particle size which is greater than or equal to the thickness of the adhesive layer.

27. The absorbent article according to claim 26 wherein the non-tacky irregularly shaped particles have an average particle size which is between 100 to 200% of the adhesive thickness.

28. An absorbent article comprising an absorbent body-facing surface, a fluid impervious garment-facing surface, a layer of pressure sensitive adhesive on at least a portion of the garment-facing surface, and a layer of non-tacky irregularly shaped particles adhered to the pressure sensitive adhesive in an amount effective to detackify the pressure sensitive adhesive upon the application of light pressure thereto, wherein the layer of pressure sensitive adhesive is applied as a layer having a thickness of about 1 to 3 mils, and wherein the non-tacky irregularly shaped particles have an average particle size which is less than the thickness of the adhesive layer.

29. An absorbent article comprising an absorbent body-facing surface, a fluid impervious garment-facing surface, a layer of pressure sensitive adhesive on at least a portion of the garment-facing surface, and a layer of non-tacky irregularly shaped particles adhered to the pressure sensitive adhesive in an amount effective to detackify the pressure sensitive adhesive upon the application of light pressure thereto, wherein the layer of pressure sensitive adhesive is applied as a layer having a thickness of about 1 to 3 mils, and wherein the non-tacky irregularly shaped material has an average particle size which is greater than or equal to the thickness of the adhesive layer.

30. The absorbent article according to claim 1 wherein the non-tacky irregularly shaped particles are organic non-tacky particles which are applied in a liquid state in the form of discrete, non-tacky dots across the surface of the adhesive.

31. The absorbent article according to claim 1 wherein the non-tacky irregularly shaped particles are organic non-tacky particles which are applied in a continuous or discontinuous thin line across the surface of the adhesive.

32. The absorbent article according to claim 1 wherein the detackified pressure sensitive adhesive has an adhesion level of at least 0.2 lb.

33. The absorbent article according to claim 1 wherein the detackified pressure sensitive adhesive has a surface area of at least 4 sq. inches.

* * * * *